United States Patent
Qi et al.

(10) Patent No.: US 9,085,501 B2
(45) Date of Patent: Jul. 21, 2015

(54) PROCESSES FOR INCREASING THE YIELD OF ETHYLENE AND PROPYLENE

(75) Inventors: Guozhen Qi, Shanghai (CN); Zhe Yang, Beijing (CN); Huiming Zhang, Shanghai (CN); Li Wang, Shanghai (CN); Ju Wang, Shanghai (CN); Xiaohong Li, Shanghai (CN); Huawen Wang, Shanghai (CN)

(73) Assignees: China Petroleum & Chemical Corporation, Beijing (CN); Shanghai Research Institute of Petrochemical Technology, Sinopec, Shanghai (CN)

( * ) Notice: Subject to any disclaimer, the term of this patent is extended or adjusted under 35 U.S.C. 154(b) by 810 days.

(21) Appl. No.: 13/298,115

(22) Filed: Nov. 16, 2011

(65) Prior Publication Data

US 2012/0123175 A1    May 17, 2012

(30) Foreign Application Priority Data

Nov. 17, 2010  (CN) .......................... 2010 1 0552720
Nov. 17, 2010  (CN) .......................... 2010 1 0553799

(51) Int. Cl.
| | | |
|---|---|---|
| C07C 1/20 | (2006.01) |
| B01J 38/30 | (2006.01) |
| B01J 38/38 | (2006.01) |
| B01J 29/85 | (2006.01) |
| B01J 29/90 | (2006.01) |

(52) U.S. Cl.
CPC . *C07C 1/20* (2013.01); *B01J 29/85* (2013.01); *B01J 29/90* (2013.01); *B01J 38/30* (2013.01); *B01J 38/38* (2013.01); *C07C 2529/85* (2013.01)

(58) Field of Classification Search
CPC ............ C07C 1/20; C07C 1/24; C07C 11/04; C07C 11/06; C07C 2529/85; B01J 8/1836

USPC .................................. 585/638, 639, 640, 925
See application file for complete search history.

(56) References Cited

U.S. PATENT DOCUMENTS

| | | | |
|---|---|---|---|
| 4,071,573 A * | 1/1978 | Owen et al. .................... | 585/402 |
| 4,499,327 A | 2/1985 | Kaiser | |
| 6,023,005 A * | 2/2000 | Lattner et al. .................. | 585/639 |

(Continued)

FOREIGN PATENT DOCUMENTS

| | | |
|---|---|---|
| CN | 1723262 | 1/2006 |
| CN | 101270017 A | 9/2008 |
| CN | 101293660 A | 10/2008 |

(Continued)

OTHER PUBLICATIONS

Zhao at al., "Technology in Progress in Increasing Propylene Production", *Guangzhou Chemical Industry*, 31(1):19, 36-39 (2004).

*Primary Examiner* — In Suk Bullock
*Assistant Examiner* — Sharon Pregler
(74) *Attorney, Agent, or Firm* — Finnegan, Henderson, Farabow & Garrett & Dunner, LLP

(57) ABSTRACT

A process for increasing the yield of ethylene and propylene, comprising:
(1) feeding a feedstock into a reaction zone with a catalyst to produce (i) a product stream and a catalyst to be regenerated;
(2) stripping and then dividing the catalyst to be regenerated into at least two parts, wherein a first part is recycled into the reaction zone at a first position, and a second part is regenerated in the regenerator to form a regenerated catalyst and then recycled into the reaction zone at a second position; and
(3) controlling the temperature increase in the reaction zone.

10 Claims, 2 Drawing Sheets

(56) References Cited

U.S. PATENT DOCUMENTS 6,166,282 A 12/2000 Miller
2004/0186333 A1* 9/2004 Lattner .................. 585/639

FOREIGN PATENT DOCUMENTS

| CN | 101357874 A | 2/2009 |
| WO | WO 2004/037950 | 5/2004 |

* cited by examiner

PROCESSES FOR INCREASING THE YIELD OF ETHYLENE AND PROPYLENE

This application claims priority under 35 U.S.C. §119 to Chinese Patent Application Nos. 201010553799.9 and 201010552720.0, filed Nov. 17, 2010.

The present disclosure relates to processes for increasing the yield of ethylene and/or propylene.

Light olefins, i.e. ethylene and propylene, are important basic chemical materials with an increasing demand. Generally, ethylene and propylene are produced from petroleum. Due to limited supply and high price of petroleum resources, the cost of producing ethylene and propylene from petroleum is continuously increasing. Recently, techniques for preparing ethylene and propylene by converting petroleum alternatives have been developed. Oxygen-containing compounds, such as alcohols (for example, methanol and ethanol), ethers (for example, dimethyl ether and methyl ethyl ether), and esters (for example, dimethyl carbonate and methyl fomlate), can be converted from petroleum alternatives, such as coal, natural gas and biomass. Some oxygen-containing compounds, such as methanol, can be produced from coal or natural gas on a large scale, reaching to production scales of, for example, millions of tons. Due to the abundant supply of such oxygen-containing compounds, in combination with the more economically efficient technique of olefin production by converting petroleum alternatives, Oxygenate To Olefins (OTO) processes, such as Methanol to Olefins (MTO) processes, have drawn more and more attention. Examples of such processes are disclosed in U.S. Pat. Nos. 4,499,327 and 6,166,282, and Chinese Patent No. CN1723262.

Nevertheless, these approaches may produce ethylene and propylene in low yield, and thus there is still a need for processes with improved yields to solve such problem.

Disclosed herein are processes for increasing the yield of ethylene and/or propylene. Such processes are used for production of ethylene and propylene, and can have advantages of higher yield of light olefins in the product.

The process disclosed herein comprises:

(1) feeding a feedstock comprising methanol into a reaction zone, and contacting the feedstock with a catalyst comprising at least one silicon-aluminophosphate molecular sieve to produce (i) a product stream comprising ethylene and/or propylene, and (ii) a catalyst to be regenerated;

(2) stripping and then dividing the catalyst to be regenerated into at least two parts, wherein a first part is recycled into the reaction zone, and a second part is fed into a regenerator to form a regenerated catalyst; and the regenerated catalyst is fed into the reaction zone at a second position; and (3) controlling the temperature increase in the reaction zone, comprising (i) vaporizing the feedstock in a vaporizer, and then dividing the feedstock comprising methanol into at least two parts: a first part is fed into the reaction zone at at least one separate position in the axial direction of the reaction zone, and a second part is heated in a heater and then fed into the reaction zone at the bottom of the reaction zone; or (ii) one part of the catalyst to be regenerated is additionally separated and is cooled and then recycled into the reaction zone at a third position, which is at about ⅕ to about ⅗ of the reaction zone height, wherein the difference between the third position and the position at which the regenerated catalyst is fed into the reaction zone (i.e., the second position) is less than about ⅙ of the reaction zone height.

In an embodiment, disclosed herein is a process for increasing the yield of ethylene and/or propylene, comprising:

(1) feeding the feedstock comprising methanol into the reaction zone, and contacting the feedstock with a catalyst comprising at least one silicon-aluminophosphate molecular sieve to produce (i) the product stream comprising ethylene and/or propylene and (ii) a catalyst to be regenerated;

(2) stripping and then dividing the catalyst to be regenerated into at least three parts, wherein the first part is recycled into the reaction zone at the bottom of the reaction zone;

the second part is fed into the regenerator to form the regenerated catalyst having a carbon deposit amount ranging from about 0.01 wt % to about 2.5 wt %, and the regenerated catalyst is degassed and fed into the reaction zone at a second position; and the third part is cooled and recycled into the reaction zone at the third position, which is at about ⅕ to about ⅗ of the reaction zone height, wherein the difference between the second position and the third position is less than about ⅙ of the reaction zone height, and the temperature difference between an inlet and an outlet of the reaction zone ranges from about 4° C. to about 20° C.

In the process disclosed herein, the silico-aluminophosphate molecular sieve, which is selected, for example, from at least one of SAPO-5, SAPO-11, SAPO-17, SAPO-18, SAPO-34, SAPO-35, SAPO-44 and SAPO-56, such as SAPO-34. In some embodiments, the reaction in the reaction zone is conducted under the conditions of a gauge pressure ranging from about 0.01 MPa to about 0.3 MPa, an average temperature ranging from about 400° C. to about 500° C., an average carbon deposit amount of the catalyst ranging from about 1.5 wt. % to about 3.5 wt. %. The catalyst to be regenerated is divided into at least three parts, wherein the first part recycled into the reaction zone at the bottom of the reaction zone comprises about 30 wt % to about 50 wt % of the catalyst; the second part fed to the regenerator for regeneration comprises about 20 wt % to about 50 wt % of the catalyst; and the third part recycled into the reaction zone at about ⅕ to about ⅗ of the reaction zone height comprises about 20 wt % to about 30 wt % of the catalyst. In some embodiments, the third part of the catalyst to be regenerated is cooled down by a heat exchanger with cooling coil pipes and then recycled into the reaction zone.

The temperature difference between the inlet and the outlet of the reaction zone is calculated by subtracting the inlet temperature from the outlet temperature.

It is well known in the art that, during the conversion of methanol into light olefins, accumulation of a certain amount of carbon deposit on the catalyst is beneficial for increasing the selectivity of light olefins in the product stream, such as about 1% to about 4%. In the process disclosed herein, in some embodiments, the feedstock comprising methanol is first in contact with the catalyst to be regenerated after being fed into the reaction zone, so as to produce light olefins in a high selectivity. The product stream and the unreacted methanol are then in contact with a mixture of the regenerated catalyst and the catalyst to be regenerated, to convert the unreacted methanol. Meanwhile, the region of the reaction zone to which the regenerated catalyst is recycled or higher regions have a lower amount of methanol in need of conversion, and therefore less reaction heat is released therein. In addition, the third part of the catalyst to be regenerated is cooled down and recycled around such regions. Such process can thus effectively control the temperature increase in the reaction zone in an advantageous state for the production of light olefins, so as to increase the yield of light olefins. By using the process disclosed herein, the yield of carbon radicals in light olefins can, for example, be 84.17 wt. %, which is 5% higher than that in the prior art, thus achieving better technical effects.

In another embodiment, disclosed herein is a process for increasing the yield of ethylene and/or propylene, comprising (1) dividing the feedstock comprising methanol after being vaporized with a vaporizer into at least two parts, wherein a first part is fed into the reaction zone at at least one separate position in the axial direction of the reaction zone; a second part is heated in a heater and fed into the bottom of the reaction zone, and is in contact with a catalyst to produce (i) a product stream comprising at least one light olefin and (ii) a catalyst to be regenerated; and (2) stripping and then dividing the catalyst to be regenerated into at least two parts, wherein a first part is recycled into the reaction zone; a second part is fed into the regenerator to form a regenerated catalyst, and the regenerated catalyst is recycled into the reaction zone.

In the process disclosed herein, the catalyst comprises at least one silico-aluminophosphate molecular sieve, which is, for example, selected from SAPO-5, SAPO-11, SAPO-17, SAPO-18, SAPO-34, SAPO-35, SAPO-44 and SAPO-56, such as SAPO-34. The reaction zone and the regenerator are, for example, both fluidized beds. About 5 wt % to about 60 wt % of the vaporized feedstock is fed into the reaction zone at at least two positions separated in the axial direction of the reaction zone at a temperature ranging from about 80° C. to about 135° C., and about 40 wt % to about 95 wt % of the vaporized feedstock is heated in the heater and fed into the bottom of the reaction zone at a temperature ranging from about 160° C. to about 250° C. The reaction in the reaction zone is conducted under the conditions of a gauge pressure ranging from about 0.01 MPa to about 0.3 MPa, an average temperature ranging from about 400° C. to about 500° C., a gaseous phase linear speed ranging from about 0.8 m/s to about 3.0 m/s, and an average carbon deposit amount of the at least one catalyst ranging from about 1.5 wt. % to about 3.5 wt. %. About 50 wt % to about 80 wt % of the catalyst to be regenerated is recycled into the bottom of the reaction zone, and about 20 wt % to about 50 wt % of the catalyst to be regenerated is regenerated in the regenerator. The regenerated catalyst is recycled into the reaction zone at a position which is at about ¼ to about ¾ of the reaction zone height. The first part of the vaporized feedstock is fed into the reaction zone at at least two positions, which are separated in the axial direction of the reaction zone and are at about ¼ to about ¾ of the reaction zone height.

In the process disclosed herein, the feedstock is fed into the reaction zone at different temperatures and at different positions. The feedstock fed from the bottom and having a higher temperature is in contact with the catalyst to be regenerated to produce light olefins in a high selectivity, and meanwhile maintains the temperature at the bottom zone of the reaction zone. The feedstock fed from multiple positions separated in the axial direction of the reaction zone and having a lower temperature may balance the temperature in the reaction zone. In some embodiments, these multiple positions are located closely to where the regenerated catalyst is recycled to the reaction zone. Since this low-temperature part of the feedstock has a strong function of balancing the heat released by the conversion reaction in the reaction zone, it will effectively decrease the temperature increase in the reaction zone and provide better conditions for the production of light olefins. In addition, the lower temperature of the feedstock can reduce the possibility of the feedstock being decomposed into inorganic gas, which will further increase the yield of light olefins. Therefore, the process disclosed herein can effectively increase the yield of light olefins. For example, the yield of carbon radicals in light olefins may be about 84.27 wt. %, which is 2% higher than that in the prior art. Thus a better technical effect can be achieved by using the process disclosed herein.

In the present disclosure, the carbon deposit amount is calculated by dividing the mass of carbon deposit on the at least one catalyst by the mass of the at least one catalyst. The mass of carbon deposit on the at least one catalyst is determined by homogeneously mixing the catalysts with carbon deposited thereon, then weighing a certain mass of the catalysts with carbon deposited thereon, combusting in a high temperature carbon analyzer, and then determining the mass of carbon dioxide produced by combustion.

In some embodiments, the silicon-aluminophosphate molecular sieves used herein are prepared by: preparing a mixed solution having a molar ratio of 0.03-0.6 R:(0.01-0.98 Si: 0.01-0.6 Al: 0.01-0.6 P): 2-500 $H_2O$, wherein R is a template agent, and crystallizing the solution at a temperature, ranging, e.g., from about 100° C. to about 250° C., and for a period of time, ranging, e.g., from about 1 h to about 10 h, to obtain a molecular sieve precursor; hydrothermally crystallizing the resultant molecular sieve precursor at a temperature ranging from about 110° C. to about 260° C. for at least 0.1 h, to obtain the final SAPO molecular sieves; and mixing the resulting molecular sieves with at least one binder in certain ratio, spray-drying and calcining the mixture to obtain the final SAPO catalyst, wherein the binder is generally in an amount ranging from about 10 wt. % to 90 wt. % of the molecular sieves.

BRIEF DESCRIPTION OF THE DRAWINGS

In FIG. 1, 1 represents the feeding pipe for the feedstock;
2 represents the reaction zone;
3 represents the gas-solid fast separation device;
4 represents the stripping zone;
5 represents the second circulating sloped pipe for the cooled catalyst to be regenerated;
6 represents the first sloped pipe for the catalyst to be regenerated;
7 represents the heat exchanger;
8 represents the gas-solid cyclone separator;
9 represents the settling zone;
10 represents the gas collecting chamber;
11 represents the outlet pipe for the gaseous phase product stream;
12 represents the second sloped pipe for the regenerated catalyst; and
13 represents the first circulating sloped pipe for the catalyst to be regenerated.

Figure 1:
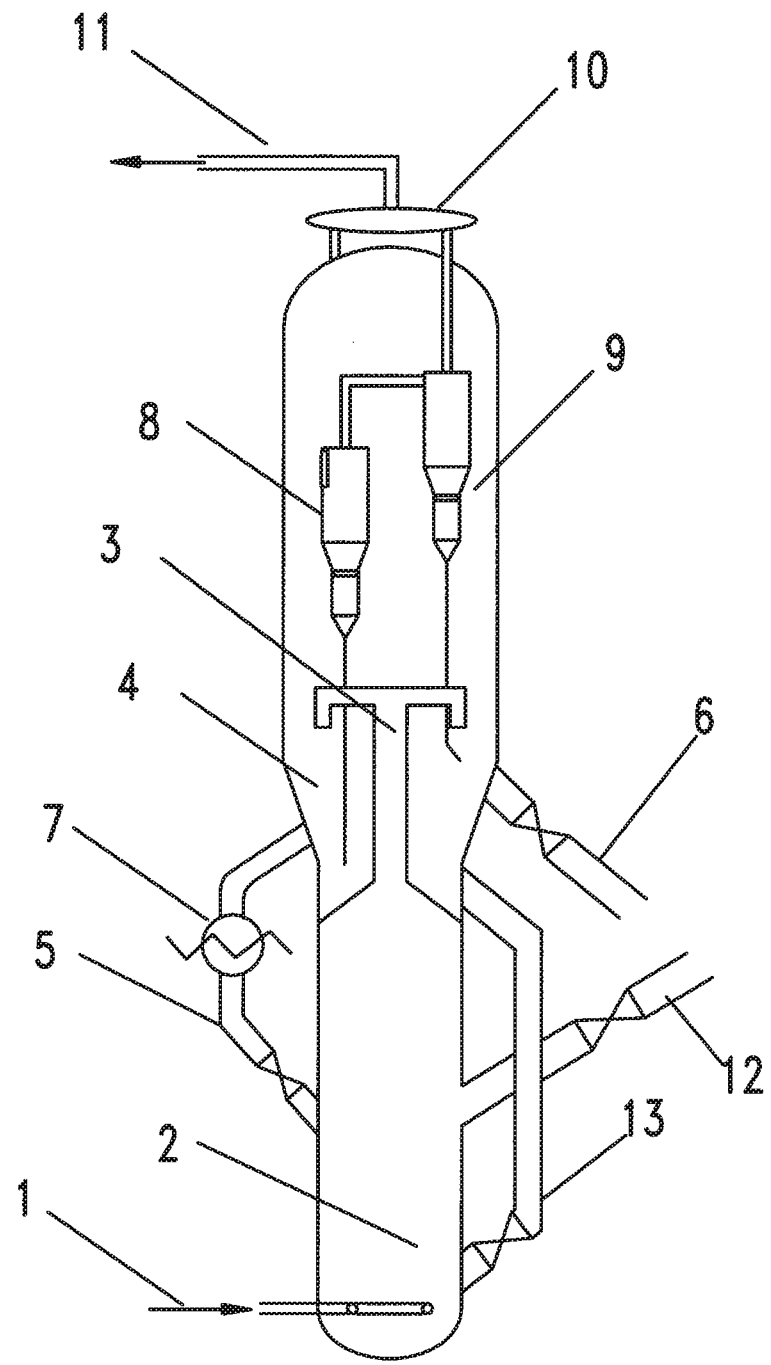
FIG. 1 is a schematic view of a reactor model used in a process according to an embodiment of the present disclosure.

In an embodiment of the present disclosure shown in FIG. 1, a feedstock comprising methanol is fed into a reaction zone 2 via a feeding pipe 1, and in contact with at least one catalyst to produce (i) a product stream comprising ethylene and propylene and (ii) a catalyst to be regenerated. The product stream with the catalyst to be regenerated passes through a gas-solid fast separation device 3 and is fed into a settling zone 9. Most of the catalyst separated by the gas-solid fast separation device 3 is fed into a stripping zone 4. The gaseous phase product stream and a part of the catalyst unseparated by the gas-solid fast separation device 3 are further separated by a gas-solid cyclone separator 8. The further separated catalyst is recycled into the stripping zone 4 via a dipleg of the gas-solid cyclone separator 8, and the gaseous phase product stream is fed into a gas collecting chamber 10, and into a subsequent separation section via an outlet pipe 11. After stripping, the catalyst to be regenerated separated by the gas-solid fast separation device 3 and the cyclone separator 8 is divided into at least three parts, wherein a first part is recycled into the bottom of the reaction zone 2 via a first circulating sloped pipe 13; a second part is fed into a regenerator via a first sloped pipe 6, and regenerated by carbon burning to form a regenerated catalyst; the regenerated catalyst is recycled into the reaction zone 2 via a second sloped pipe 12; and a third part is heat-exchanged via a heat exchanger 7, and recycled into the reaction zone 2 via a second circulating sloped pipe 5.

Figure 2:
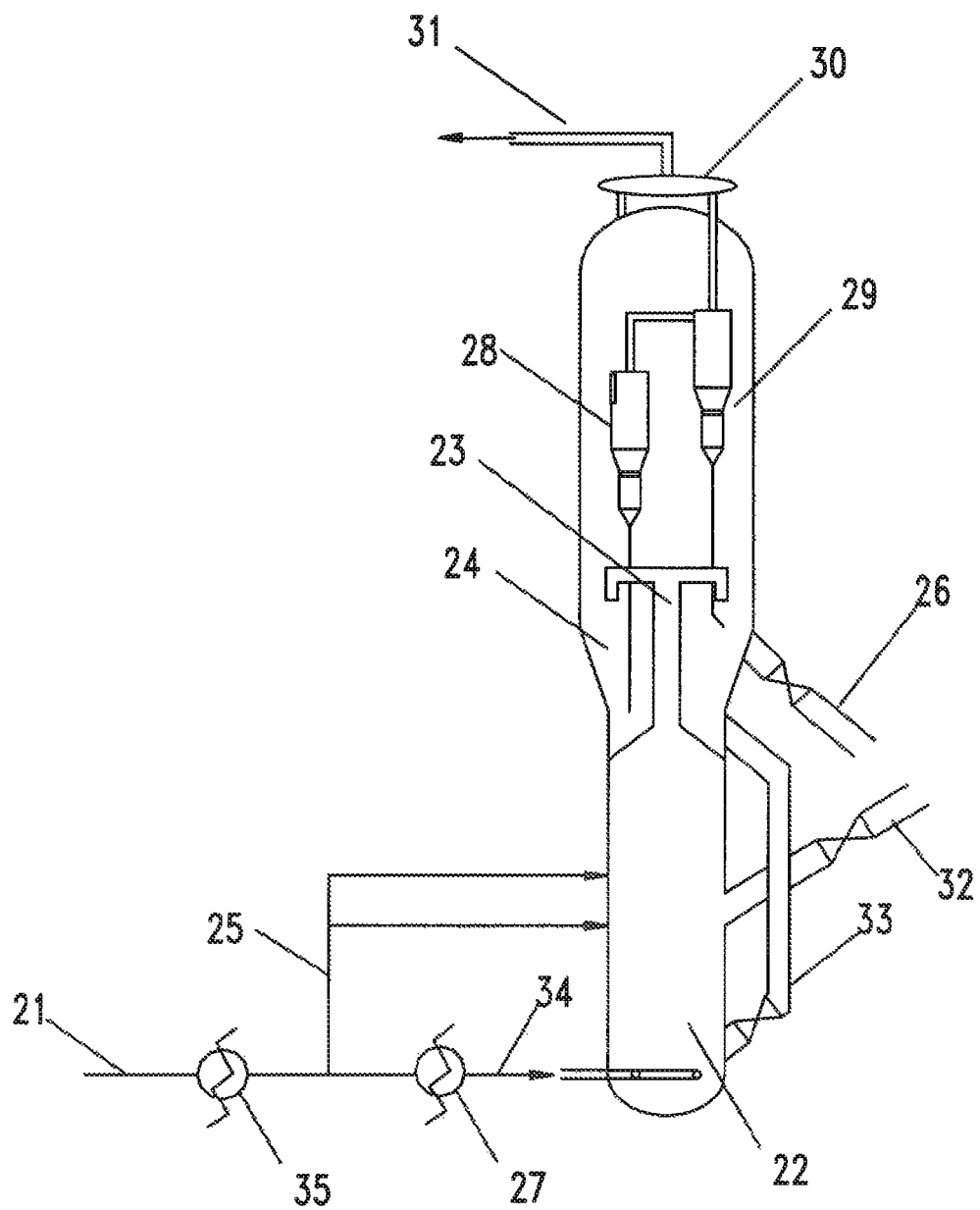
FIG. 2 is a schematic view of a reactor model used in a process according to another embodiment of the present disclosure.

In FIG. 2,

21 represents a liquid feedstock;

22 represents a reaction zone;

23 represents a gas-solid fast separation device;

24 represents a stripping zone;

25 represents a first feeding pipe for feeding the vaporized feedstock in the axial direction;

26 represents a first sloped pipe for the catalyst to be regenerated;

27 represents a heat exchanger;

28 represents a gas-solid cyclone separator;

29 represents a settling zone;

30 represents a gas collecting chamber;

31 represents an outlet pipe for the gaseous phase product stream;

32 represents a second sloped pipe for the regenerated catalyst;

33 represents a circulating sloped pipe for the catalyst to be regenerated;

34 represents a second feeding pipe for feeding the heated feedstock.

35 represents a vaporizer.

In another embodiment of the present disclosure shown in FIG. 2, a liquid feedstock is fed into a vaporizer 35 and divided into two parts, wherein a first part is fed via a first feeding pipe 25 into a reaction zone 22 at at least one separate position in the axial direction of the reaction zone 22; a second part is heated by a heat exchanger 27, and fed via a second feeding pipe 34 into the bottom of the reaction zone 22, and in contact with at least one catalyst to produce (i) a product stream comprising ethylene and propylene as well as (ii) a catalyst to be regenerated. The product stream with the catalyst to be regenerated passes through a gas-solid fast separation device 23 and is fed into a settling zone 29. Most of the catalyst separated by the gas-solid fast separation device 23 is fed into a stripping zone 24. The gaseous phase product stream and a part of the catalyst unseparated by the gas-solid fast separation device 23 are further separated by a gas-solid cyclone separator 28. The further separated catalyst is recycled to a stripping zone 24 via a dipleg of the gas-solid cyclone separator 28, and the gaseous phase product stream is fed into a gas collecting chamber 30, and into a subsequent separation section via an outlet pipe 31. After stripping, the catalyst to be regenerated separated by the gas-solid fast separation device 23 and the cyclone separator 28 is divided into at least two parts, wherein a first part is recycled to the reaction zone 22 via a circulating sloped pipe 33; a second part is fed into a regenerator via a first sloped pipe 26 and regenerated by carbon burning to form a regenerated catalyst; the regenerated catalyst is recycled to the reaction zone 22 via a second sloped pipe 32.

The present disclosure is further illustrated by the following examples, but is not limited to the following examples.

EXAMPLES

Examples 1 and 2

In a small-scale fluidized bed reaction and a regeneration device, the reactor model used in a process according to an embodiment of the present disclosure is shown in FIG. 1. The feedstock was pure methanol. The type of the at least one catalyst is shown in Table 1. The catalyst was prepared by the process disclosed in Chinese Patent Application No. CN200810043289.X, wherein the binder used for forming the molecule sieve was aluminum sol, and the amount of the molecule sieve in the catalyst was 70 wt. %. The reaction in the reaction zone was conducted under the conditions of a gauge pressure of 0.1 MPa, an average temperature of 475° C., and an average carbon deposit amount on the catalyst of 3.0 wt %. The catalyst to be regenerated was divided into at least three parts, wherein a first part comprising 50% of the catalyst to be regenerated was recycled to the bottom of the reaction zone; a second part comprising 30% of the catalyst to be regenerated was regenerated in a regenerator; a third part comprising 20% of the catalyst to be regenerated was recycled at about ⅗ of the reaction zone height. The third part of the catalyst to be regenerated was cooled down by a heat exchanger with cooling coil pipes and recycled into the reaction zone. The regenerated catalyst had a carbon deposit mass percentage of 1.25%. After degassing, the regenerated catalyst was fed into the reaction zone at ⅗ of the reaction zone height, to maintain the stability of the catalyst flow control. The product stream at the outlet of the reactor was analyzed by online gas chromatography. The reaction results are shown in Table 1.

TABLE 1

| | Parameters | | |
|---|---|---|---|
| | Type of Catalyst | Yield of carbon radicals in light olefins, wt. % | Temperature difference between the inlet and the outlet of the reaction zone, ° C. |
| Example 1 | SAPO-18 | 80.64 | 8 |
| Example 2 | SAPO-34 | 83.15 | 11 |

Examples 3-4

Reactions were conducted according to the conditions and steps described in Example 2, except for the average temperature in the reaction zone. The reaction results are shown in Table 2.

TABLE 2

| | Parameters | | |
|---|---|---|---|
| | Average temperature in the reaction zone, ° C. | Yield of carbon radicals in light olefins, wt. % | Temperature difference between the inlet and the outlet of the reaction zone, ° C. |
| Example 3 | 400 | 79.15 | 18 |
| Example 4 | 500 | 82.96 | 9 |

Examples 5-6

Reactions were conducted according to the conditions and steps described in Example 2, except for the reaction pressure. The reaction results are shown in Table 3.

TABLE 3

| | Parameters | | |
|---|---|---|---|
| | Gauge reaction pressure, MPa | Yield of carbon radicals in light olefins, wt. % | Temperature difference between the inlet and the outlet of the reaction zone, ° C. |
| Example 5 | 0.3 | 78.87 | 20 |
| Example 6 | 0.01 | 84.17 | 4 |

Example 7

Reactions were conducted according to the conditions and steps described in Example 2 with the following exceptions. The average carbon deposit amount on the catalyst was 3.5 wt. %, and the gauge pressure of the reaction was 0.08 MPa. The catalyst to be regenerated was divided into at least three parts, wherein a first part comprising 30% of the catalyst to be regenerated was recycled into the bottom of the reaction zone; a second part comprising 50% of the catalyst to be regenerated was regenerated in the regenerator; a third part comprising 20% of the catalyst to be regenerated was recycled at ⅔ of the reaction zone height. The third part of the catalyst to be regenerated was cooled down by a heat exchanger with cooling coil pipes and recycled into the reaction zone. The regenerated catalyst had a carbon deposit mass percent of 2.5%. After degassing, the regenerated catalyst was fed into the reaction zone at ½ of the reaction zone height. The product stream at the outlet of the reactor was analyzed by online gas chromatography. The yield of carbon radicals in light olefins was 83.02 wt. %, and the temperature difference between the inlet and the outlet of the reaction zone was 6° C.

Example 8

Reactions were conducted according to the conditions and steps described in Example 2 with the following exceptions. The average carbon deposit amount on the catalyst was 1.5 wt. %, and the gauge pressure of the reaction was 0.2 MPa, The catalyst to be regenerated was divided into at least three parts, wherein a first part comprising 30 wt % of the catalyst was recycled into the bottom of the reaction zone; a second part comprising 40 wt % of the catalyst was regenerated in the regenerator; a third part comprising 30% of the catalyst to be regenerated was recycled at ⅔ of the reaction zone height. The third part of the catalyst to be regenerated was cooled down by a heat exchanger with cooling coil pipes and recycled to the reaction zone. The regenerated catalyst had a carbon deposit mass percent of 0.015%. After degassing, the regenerated catalyst was fed into the reaction zone at ½ of the reaction zone height. The product stream at the outlet of the reactor was analyzed by online gas chromatography. The yield of carbon radicals in light olefins was 81.36 wt. %, and the temperature difference between the inlet and the outlet of the reaction zone was 12° C.

Example 9

In the fluidized bed reaction and regeneration device, the reactor model used in a process according to another embodiment of the present disclosure is shown in FIG. 2, and the reaction zone and the regenerator both are fluidized beds. The feedstock was pure methanol, and the catalyst was SAPO-34. The reaction in the reaction zone was conducted under the conditions of a gauge pressure of 0.1 MPa, an average temperature of 475° C., a gaseous phase linear speed of 1.35 m/s, and an average carbon deposit amount of the catalyst of 2.5 wt. %. Medium-pressure vapor was used in the vaporizer to vaporize the methanol feedstock, and high-pressure vapor was used in the heat exchanger to heat the methanol feedstock. 20% of the feedstock vaporized in the vaporizer was fed at 115° C. at two positions, i.e., at ¼ and ½ of the reaction zone height, and separated in the axial direction of the reaction zone, wherein the feeding rate at the two positions were the same. 80% of the feedstock vaporized in the vaporizer was heated in the heat exchanger, fed at 200° C. into the bottom of the reaction zone and in contact with the catalyst. The catalyst to be regenerated formed therein was stripped, wherein 70 wt % of the catalyst was recycled into the bottom of the reaction zone, and 30 wt % of the catalyst was fed into the regenerator for regeneration. The regenerated catalyst was fed at ½ of the reaction zone height, to maintain the stability of the catalyst flow control. The product stream at the outlet of the reactor was analyzed by online gas chromatography, and the yield of carbon radicals in light olefins was 83.59 wt. %.

Example 10

Reactions were conducted according to the conditions and steps as described in Example 9 with the following exceptions. The reaction in the reaction zone was conducted under the conditions of a gauge pressure of 0.01 MPa, an average temperature of 500° C., a gaseous phase linear speed of 3.0 m/s, and an average carbon deposit amount of the catalyst of 3.5 wt. %. 60% of the feedstock vaporized in the vaporizer was fed at 135° C. at one position, i.e. at ¼ of the reaction zone height, separated in the axial direction of the reaction zone, 40% of the feedstock vaporized in the vaporizer was heated in the heat exchanger, fed at 250° C. into the bottom of the reaction zone and in contact with the catalyst. The catalyst to be regenerated formed therein was stripped, wherein 50 wt % of the catalyst was recycled into the bottom of the reaction zone, and 50 wt % of the catalyst was fed into the regenerator for regeneration. The regenerated catalyst was fed at ¼ of the reaction zone height, to maintain the stability of the catalyst flow control. The product stream at the outlet of the reactor was analyzed by online gas chromatography, and the yield of carbon radicals in light olefins was 84.05 wt. %.

Example 11

Reactions were conducted according to the conditions and steps described in Example 9 with the following exceptions. The reaction in the reaction zone was conducted under the conditions of a gauge pressure of 0.3 MPa, an average temperature of 400° C., a gaseous phase linear speed of 0.8 m/s, and an average carbon deposit amount of the catalyst of 1.5 wt. %. 5% of the feedstock vaporized in the vaporizer was fed at 80° C. at one position, i.e. at ¾ of the reaction zone height, separated in the axial direction of the reaction zone. 95% of the feedstock vaporized in the vaporizer was heated in the heat exchanger, fed at 160° C. into the bottom of the reaction zone and in contact with the catalyst. The catalyst to be regenerated formed therein was stripped, wherein 80 wt % of the catalyst to be regenerated was recycled into the bottom of the reaction zone, and 20 wt % of the catalyst to be regenerated was fed into the regenerator for regeneration. The regenerated catalyst was fed at ¾ of the reaction zone height, to maintain the stability of the catalyst flow control. The product stream at the outlet of the reactor was analyzed by online gas chromatography, and the yield of carbon radicals in light olefins was 81.11 wt. %.

Example 12

Reactions were conducted according to the conditions and steps described in Example 9 with the following exceptions. The reaction in the reaction zone was conducted under the conditions of a gauge pressure of 0.15 MPa, an average temperature of 470° C., a gaseous phase linear speed of 1.25 m/s, and an average carbon deposit amount of the catalyst of 3.0 wt %. 45% of the feedstock vaporized in the vaporizer was fed at 100° C. at three positions, i.e., ¼, ½ and ¾ of the reaction zone height, and separated in the axial direction of the reaction zone. 55% of the feedstock vaporized in a vaporizer was heated in the heat exchanger, fed at 190° C. into the bottom of the reaction zone and in contact with the catalyst. The catalyst to be regenerated formed therein was stripped, wherein 60 wt % of the catalyst was recycled into the bottom of the reaction zone, and 40 wt % of the catalyst was fed into the regenerator for regeneration. The regenerated catalyst was fed at ½ of the reaction zone height, to maintain the stability of the catalyst flow control. The product stream at the outlet of the reactor was analyzed by online gas chromatography, and the yield of carbon radicals in light olefins was 84.27 wt. %.

What is claimed is:

1. A process for increasing the yield of ethylene and/or propylene, comprising:
   (1) feeding a feedstock comprising methanol into a reaction zone, and contacting the feedstock with a catalyst comprising at least one silicon-aluminophosphate molecular sieve to produce (i) a product stream comprising ethylene and/or propylene, and (ii) a catalyst to be regenerated;
   (2) stripping and then dividing the catalyst to be regenerated into at least two parts, wherein a first part is recycled into the reaction zone at a first position, a second part is regenerated in a regenerator to form a regenerated catalyst, and the regenerated catalyst is recycled into the reaction zone at a second position; and
   (3) controlling the temperature increase in the reaction zone, comprising (i) vaporizing the feedstock with a vaporizer, and then dividing the feedstock into at least two parts, wherein a first part is fed into the reaction zone at at least one separate position in the axial direction of the reaction zone, and a second part is heated in a heater and then fed into the reaction zone at the bottom of the reaction zone, and wherein the first part in step (2) is recycled into the bottom of the reaction zone, and the regenerated catalyst in step (2) is recycled into the reaction zone at about ¼ to about ¾ of the reaction zone height;
   or (ii) additionally separating one part of the catalyst to be regenerated into a third part, and cooling and recycling the third part into the reaction zone at a third position, which is at about ⅕ to about ⅗ of the reaction zone height, and wherein the first part in step (2) is recycled into the bottom of the reaction zone, and the difference between the second position in step (2) and the third position is less than ⅙ of the reaction zone height.

2. The process according to claim 1, comprising:
   (1) feeding the feedstock comprising methanol into the reaction zone, contacting with the catalyst to produce (i) the product stream comprising ethylene and/or propylene, and (ii) the catalyst to be regenerated;
   (2) stripping and then dividing the catalyst to be regenerated into at least three parts, wherein:
   the first part is recycled into the bottom of the reaction zone;
   the second part is regenerated in the regenerator to form the regenerated catalyst having a carbon deposit amount ranging from about 0.01 wt % to about 2.5 wt % and the regenerated catalyst is degassed and recycled into the reaction zone at the second position; and
   the third part is cooled down and recycled into the reaction zone at a third position, which is at about ⅕ to about ⅗ of the reaction zone height,
   wherein the difference between the second position and the third position is less than ⅙ of the reaction zone height, and the temperature difference between the inlet and the outlet of the reaction zone ranges from about 4° C. to about 20° C.

3. The process according to claim 1, wherein the at least one silico-aluminophosphate molecular sieve is selected from SAPO-5, SAPO-11, SAPO-17, SAPO-18, SAPO-34, SAPO-35, SAPO-44 and SAPO-56.

4. The process according to claim 3, wherein the at least one silicon-aluminophosphate molecular sieve is SAPO-34.

5. The process according to claim 1, wherein the reaction in the reaction zone is conducted under a gauge pressure ranging from about 0.01 MPa to about 0.3 MPa, at an average temperature ranging from about 400° C. to about 500° C., and with an average carbon deposit amount of the at least one catalyst ranging from about 1.5 wt % to about 3.5 wt %.

6. The process according to claim 2, wherein the first part comprises about 30 wt % to about 50 wt % of the catalyst to be regenerated; the second part comprises about 20 wt % to about 50 wt % of the catalyst to be regenerated; and the third part comprises about 20% to about 30 wt % of the catalyst to be regenerated.

7. The process according to claim 2, wherein the third part of the catalyst to be regenerated is cooled down by a heat exchanger with cooling coil pipes and then recycled into the reaction zone.

8. The process according to claim 1, wherein in (3)(i), about 5 wt % to about 60 wt % of the feedstock vaporized with a vaporizer is fed into the reaction zone at at least two positions separated in the axial direction of the reaction zone at a temperature ranging from about 80° C. to about 135° C., and about 40 wt % to about 95 wt % of the feedstock vaporized with a vaporizer is heated in the heater and fed into the bottom of the reaction zone at a temperature ranging from about 160° C. to about 250° C.

9. The process according to claim 1, wherein in (3)(i), about 50 wt % to about 80 wt % of the catalyst to be regenerated is recycled into the bottom of the reaction zone; and about 20 wt % to about 50 wt % of the catalyst to be regenerated is recycled into the regenerator for regeneration.

10. The process according to claim 1, wherein in (3)(i), the vaporized feedstock is fed into the reaction zone at at least two positions, which are separated in the axial direction of the reaction zone and are at about ¼ to about ¾ of the reaction zone height.

* * * * *